(12) United States Patent
Viola

(10) Patent No.: US 7,455,682 B2
(45) Date of Patent: *Nov. 25, 2008

(54) STRUCTURE CONTAINING WOUND TREATMENT MATERIAL

(75) Inventor: Frank J. Viola, Sandy Hook, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 531 days.

This patent is subject to a terminal disclaimer.

(21) Appl. No.: 11/048,353

(22) Filed: Feb. 1, 2005

(65) Prior Publication Data

US 2006/0085032 A1     Apr. 20, 2006

Related U.S. Application Data

(60) Provisional application No. 60/620,067, filed on Oct. 18, 2004.

(51) Int. Cl.
    *A61B 17/04* (2006.01)
(52) U.S. Cl. .............. 606/219; 227/179.1; 227/178.1; 227/19
(58) Field of Classification Search .............. 227/179.1, 227/178.1, 19, 175.1; 606/219, 214
    See application file for complete search history.

(56) References Cited

U.S. PATENT DOCUMENTS

| 3,079,606 | A | 3/1963 | Bobrov et al. |
| 3,490,675 | A | 1/1970 | Green et al. |
| 3,499,591 | A | 3/1970 | Green |
| 4,392,493 | A | 7/1983 | Niemeijer |
| 4,429,695 | A | 2/1984 | Green |
| 4,573,468 | A | 3/1986 | Conta et al. |
| 4,672,969 | A | 6/1987 | Dew |
| 5,065,929 | A | 11/1991 | Schulze et al. |
| 5,119,983 | A | 6/1992 | Green et al. |
| 5,156,614 | A | 10/1992 | Green et al. |
| 5,342,395 | A * | 8/1994 | Jarrett et al. ............ 606/219 |
| 5,385,606 | A | 1/1995 | Kowanko |
| 5,403,312 | A | 4/1995 | Yates et al. |
| 5,415,159 | A | 5/1995 | Ortiz et al. |
| 5,417,687 | A | 5/1995 | Nardella et al. |
| 5,441,193 | A * | 8/1995 | Gravener ............ 227/176.1 |
| 5,531,744 | A | 7/1996 | Nardella et al. |
| 5,542,594 | A | 8/1996 | McKean et al. |

(Continued)

FOREIGN PATENT DOCUMENTS

DE       199 24 311       11/2000

(Continued)

OTHER PUBLICATIONS

European Search Report.

*Primary Examiner*—Rinaldi I. Rada
*Assistant Examiner*—Michelle Lopez

(57) ABSTRACT

According to an aspect of the present disclosure, an anvil assembly for a circular stapling apparatus, is disclosed. The anvil assembly includes an anvil head configured to support an anvil plate thereon; a shaft extending from the anvil head and configured to selectively engage a connection member of the circular stapling apparatus; an anvil plate operatively connected to the anvil head, the anvil plate defining a plurality of staple forming pockets therein; and a wound treatment material disposed in each staple forming pocket of the anvil plate. The wound treatment material is at least one of an adhesive, a sealant, a hemostat and a medicament.

16 Claims, 7 Drawing Sheets

U.S. PATENT DOCUMENTS

| | | | |
|---|---|---|---|
| 5,549,628 | A | 8/1996 | Cooper et al. |
| 5,575,803 | A | 11/1996 | Cooper et al. |
| 5,582,834 | A | 12/1996 | Leung et al. |
| 5,599,350 | A | 2/1997 | Schulze et al. |
| 5,624,452 | A | 4/1997 | Yates |
| 5,658,279 | A | 8/1997 | Nardella et al. |
| 5,669,934 | A | 9/1997 | Sawyer |
| 5,688,270 | A | 11/1997 | Yates et al. |
| 5,693,051 | A | 12/1997 | Schulze et al. |
| 5,702,409 | A | 12/1997 | Rayburn et al. |
| 5,709,680 | A | 1/1998 | Yates et al. |
| 5,716,366 | A | 2/1998 | Yates |
| 5,735,848 | A | 4/1998 | Yates et al. |
| 5,752,965 | A | 5/1998 | Francis et al. |
| 5,755,717 | A | 5/1998 | Yates et al. |
| 5,769,892 | A | 6/1998 | Kingwell |
| 5,782,914 | A | 7/1998 | Schankereli |
| 5,799,857 | A | 9/1998 | Robertson et al. |
| 5,807,393 | A | 9/1998 | Williamson, IV et al. |
| 5,810,811 | A | 9/1998 | Yates et al. |
| 5,810,855 | A | 9/1998 | Rayburn et al. |
| 5,814,057 | A | 9/1998 | Oi et al. |
| 5,817,091 | A | 10/1998 | Nardella et al. |
| 5,817,093 | A | 10/1998 | Williamson, IV et al. |
| 5,833,690 | A | 11/1998 | Yates et al. |
| 5,833,695 | A | 11/1998 | Yoon |
| 5,876,401 | A | 3/1999 | Schulze et al. |
| 5,915,616 | A | 6/1999 | Viola et al. |
| 5,964,394 | A | 10/1999 | Robertson |
| 6,003,517 | A | 12/1999 | Sheffield et al. |
| 6,024,741 | A | 2/2000 | Williamson, IV et al. |
| 6,032,849 | A | 3/2000 | Mastri et al. |
| 6,045,560 | A | 4/2000 | McKean et al. |
| 6,063,097 | A | 5/2000 | Oi et al. |
| 6,099,551 | A | 8/2000 | Gabbay |
| H1904 | H | 10/2000 | Yates et al. |
| 6,165,175 | A | 12/2000 | Wampler et al. |
| 6,239,190 | B1 | 5/2001 | Wilkinson et al. |
| 6,241,139 | B1 | 6/2001 | Milliman et al. |
| 6,250,532 | B1 | 6/2001 | Green et al. |
| 6,273,897 | B1 | 8/2001 | Dalessandro et al. |
| 6,296,640 | B1 | 10/2001 | Wampler et al. |
| 6,312,474 | B1 | 11/2001 | Francis et al. |
| 6,325,810 | B1 | 12/2001 | Hamilton et al. |
| 6,330,965 | B1 | 12/2001 | Milliman et al. |
| 6,468,275 | B1 | 10/2002 | Wampler et al. |
| 6,485,490 | B2 | 11/2002 | Wampler et al. |
| 6,491,201 | B1 | 12/2002 | Whitman |
| 6,503,257 | B2 | 1/2003 | Grant et al. |
| 6,569,173 | B1 | 5/2003 | Blatter et al. |
| 6,592,597 | B2 | 7/2003 | Grant et al. |
| 6,638,285 | B2 | 10/2003 | Gabbay |
| 6,656,193 | B2 | 12/2003 | Grant et al. |
| 6,681,979 | B2 | 1/2004 | Whitman |
| 6,695,199 | B2 | 2/2004 | Whitman |
| 7,238,195 | B2 | 7/2007 | Viola |
| 2001/0007069 | A1 | 7/2001 | Bombard et al. |
| 2002/0151911 | A1 | 10/2002 | Gabbay |
| 2002/0156150 | A1 | 10/2002 | Williams |
| 2002/0165559 | A1 | 11/2002 | Grant et al. |
| 2002/0165562 | A1 | 11/2002 | Grant et al. |
| 2002/0173558 | A1 | 11/2002 | William et al. |
| 2003/0050590 | A1 | 3/2003 | Kirsch |
| 2003/0073982 | A1 | 4/2003 | Whitman |
| 2003/0089757 | A1 | 5/2003 | Whitman |
| 2003/0183671 | A1 | 10/2003 | Mooradian et al. |
| 2004/0093029 | A1 | 5/2004 | Zubik et al. |
| 2005/0184121 | A1* | 8/2005 | Heinrich .................. 227/175.1 |
| 2005/0192628 | A1* | 9/2005 | Viola ......................... 606/219 |
| 2006/0235469 | A1* | 10/2006 | Viola ......................... 606/219 |
| 2006/0271104 | A1* | 11/2006 | Viola et al. ................. 606/214 |

FOREIGN PATENT DOCUMENTS

| | | |
|---|---|---|
| DE | 199 24 311 A1 | 11/2000 |
| EP | 0 577 373 A2 | 1/1994 |
| WO | WO 00/56376 A1 | 9/2000 |
| WO | WO 01/62158 A2 | 8/2001 |
| WO | WO 01/62162 A1 | 8/2001 |
| WO | WO 02/30297 A2 | 4/2002 |
| WO | WO 03/088844 A1 | 10/2003 |
| WO | WO 03/088845 | 10/2003 |
| WO | WO 03/094743 A1 | 11/2003 |
| WO | WO 03/094746 | 11/2003 |
| WO | WO 03/094746 A1 | 11/2003 |
| WO | WO 03/105698 | 12/2003 |
| WO | WO 03/105698 A2 | 12/2003 |

* cited by examiner

STRUCTURE CONTAINING WOUND TREATMENT MATERIAL

CROSS-REFERENCE TO RELATED APPLICATIONS

The present application claims the benefit of and priority to U.S. Provisional Application Ser. No. 60/620,067 filed on Oct. 18, 2004, the entire contents of which are incorporated herein by reference.

BACKGROUND

1. Technical Field

The present disclosure relates to surgical instruments and methods for enhancing properties of tissue repaired or joined by surgical staples and, more particularly to surgical instruments and structure configured to apply surgical mechanical fasteners concomitantly with a non-mechanical biocompatible wound treatment material to enhance the properties of repaired or adjoined tissue at a target surgical site.

2. Discussion of Related Art

Throughout the years the medical field has utilized various techniques in an effort to join or bond body tissue together. Historically, suturing was the accepted technique for rejoining severed tissues and closing wounds. Suturing was historically achieved with a surgical needle and a suturing thread, and more recently, with a variety of polymeric or metallic staples, as will be discussed below. The intended function of sutures is to hold the edges of a wound or tissue against one another during the healing process so as to reduce discomfort, pain, scarring and the time required for healing.

Recently, many procedures which in the past required conventional suturing have been replaced by staple suturing which involves the application of the staples to the edges of the wound or tissue with the use of a surgical stapler. Surgical staplers have been developed for joining adjacent tissue, for providing hemostasis of adjacent tissue and for providing hemostasis in conjunction with cutting of adjacent tissue. Such surgical staplers include both linear and annular type configurations. A typical linear stapler and cutter includes parallel rows of staples with a slot for a cutting means to travel between the rows of staples.

Typical linear type staplers are disclosed in commonly assigned U.S. Pat. No. 6,045,560 to McKean et al., U.S. Pat. No. 6,032,849 to Mastri et al., and U.S. Pat. No. 5,964,394 to Robertson, the entire contents of each of which are incorporated herein by reference. A typical annular stapler and cutter, including a plurality of annular rows of staples, typically two, and an annular blade disposed internal of the rows of staples, is disclosed in commonly assigned U.S. Pat. No. 5,799,857 to Robertson et al. and 5,915,616 to Viola et al., the entire contents of each of which are incorporated herein by reference.

These types of surgical staplers secure adjoining body tissue for improved cutting, join layers of tissue to one another and provide hemostasis by applying parallel or annular rows of staples to surrounding tissue as the cutting means cuts between the parallel or annular rows. Accordingly, by enabling a surgeon to perform all of these tasks simultaneously, surgical staplers have been effective in decreasing the amount of time it takes to fasten tissue together. To even further enhance joining and hemostasis in instances where the stapler is used in highly vascularized tissue, surgical staplers with multiple rows of staples have been used with a high degree of success.

Other surgical procedures utilize pledgets, buttresses or other types of reinforcement materials and fabrics. These buttresses are typically placed over the tissue contacting surface of the anvil and/or the tissue contacting surface of the cartridge of the surgical stapling instrument and secured against the target tissue during the firing of the surgical stapling instrument. Reference may be made to U.S. Pat. 5,542,594, the entire content of which is incorporated herein by reference, for a more detailed discussion of the use of buttresses in cooperation with surgical stapling instrument.

Still other surgical procedures involve the step of applying (e.g., by spraying, brushing, etc.) an adhesive material and/or a sealant material to the external surface of the target surgical site following the surgical stapling procedure.

Another procedure which has been developed includes the use of biological tissue adhesives have recently been developed for tissue repair and the creation of anastomoses. Generally, biological adhesives bond separated tissues together to aid in the healing process and to enhance the tissue strength. Such adhesives may be used instead of suturing and stapling for example in surgical procedures for the repair of tissue or the creation of anastomoses.

The application of a suitable biocompatible adhesive offers many advantages to the patient and the surgeon alike such as, for example, the avoidance of penetration of tissue by needles and/or staples, as well as the immediate sealing of the tissue being treated. Moreover, use of a biocompatible adhesive tends to minimize foreign body reaction and scarring.

SUMMARY

According to an aspect of the present disclosure, an anvil assembly for a circular stapling apparatus, is disclosed. The anvil assembly includes an anvil head configured to support an anvil plate thereon; a shaft extending from the anvil head and configured to selectively engage a connection member of the circular stapling apparatus; an anvil plate operatively connected to the anvil head, the anvil plate defining a plurality of staple forming pockets therein; and a wound treatment material disposed in each staple forming pocket of the anvil plate.

The anvil assembly may further include a liner covering the plurality of staple forming pockets. Desirably, the staple forming pockets are arranged in a pair of spaced apart concentric annular rings. The staple forming pockets are in registration with respective staple retaining slots formed in a staple cartridge assembly of the surgical stapling apparatus.

It is envisioned that the wound treatment material is contained in a capsule. Accordingly, each capsule is configured for retention within the staple forming pockets.

According to another aspect of the present disclosure, a circular surgical stapling apparatus for performing an anastomosis, is disclosed. The stapling apparatus includes an anvil assembly having an anvil head configured to support an anvil plate thereon; a shaft extending from the anvil head and configured to selectively engage a connection member of the circular stapling apparatus; an anvil plate operatively connected to the anvil head, the anvil plate defining a plurality of staple forming pockets therein; and a wound treatment material disposed in each staple forming pocket of the anvil plate.

The surgical stapling apparatus further includes a tubular body portion having a connection member configured to selectively engage the shaft of the anvil assembly; and a staple cartridge assembly operatively supported on a distal end of the tubular body portion. The staple cartridge assembly includes a plurality of staple retaining slots in registration with the staple forming pockets of the anvil assembly; and a staple disposed in each staple retaining slot.

The anvil assembly may include a liner covering the staple forming pockets. Desirably, the liner is capable of being penetrated by the staples when the surgical stapling apparatus is fired.

According to a further aspect of the present disclosure, a method of performing a surgical anastomosis procedure, is disclosed. The method includes the steps of providing a circular surgical stapling apparatus including an anvil assembly having an anvil head configured to support an anvil plate thereon; a shaft extending from the anvil head and configured to selectively engage a connection member of the circular stapling apparatus; an anvil plate operatively connected to the anvil head, the anvil plate defining a plurality of staple forming pockets therein; and a wound treatment material disposed in each staple forming pocket of the anvil plate. The surgical stapling apparatus further including a tubular body portion having a connection member configured to selectively engage the shaft of the anvil assembly; and a staple cartridge assembly operatively supported on a distal end of the tubular body portion. The staple cartridge assembly includes a plurality of staple retaining slots in registration with the staple forming pockets of the anvil assembly; and a staple disposed in each staple retaining slot.

The method further includes the steps of inserting the anvil assembly into a first intestinal section; inserting the staple cartridge assembly into a second intestinal section; connecting a shaft of the anvil assembly to the connection member of the tubular body portion; approximating the anvil assembly toward the staple cartridge assembly; and firing the surgical stapling apparatus to drive the staples through the first and second intestinal sections and into the staple forming pockets of the anvil assembly. Accordingly, when the staples enter the staple forming pockets the staples release the wound treatment material therefrom.

The anvil assembly may further include a liner covering the staple forming pockets. Desirably, the liner is capable of being penetrated by the staples when the surgical stapling apparatus is fired.

According to another aspect of the present disclosure, a surgical stapling apparatus including an anvil assembly configured to support an anvil plate thereon and an anvil plate operatively connected to the anvil assembly and defining a plurality of staple forming pockets therein, is provided. The improvement includes providing a wound treatment material in each staple forming pocket of the anvil plate.

Desirably, the wound treatment material is at least one of an adhesive, a sealant, a hemostat and a medicament.

The adhesive includes at least one of an adhesive which cures upon tissue contact, an adhesive which cures upon exposure to ultraviolet (UV) light, and an adhesive which is pressure sensitive. The may also include at least one of a protein derived, aldehyde-based adhesive material, and a cyanoacrylate-based material.

The sealant material includes at least one of a fibrin sealant material, a collagen-based and synthetic polymer-based tissue sealant material, and synthetic polyethylene glycol-based, hydrogel sealant material.

The hemostat material includes at least one of a fibrin-based material, a collagen-based material, an oxidized regenerated cellulose-based material, a gelatin-based material, and a fibrinogen-thrombin material.

The medicament includes at least one of drugs, enzymes, growth factors, peptides, proteins, dyes, and diagnostic agents.

BRIEF DESCRIPTION OF THE DRAWINGS

The foregoing features of the present disclosure will become more readily apparent and may be understood by referring to the following detailed description of an illustrated embodiment of a surgical instrument, apparatus or structure, taken in conjunction with the accompanying drawings, in which.

DETAILED DECRIPTION OF THE EMBODIMENT

Figure 1:
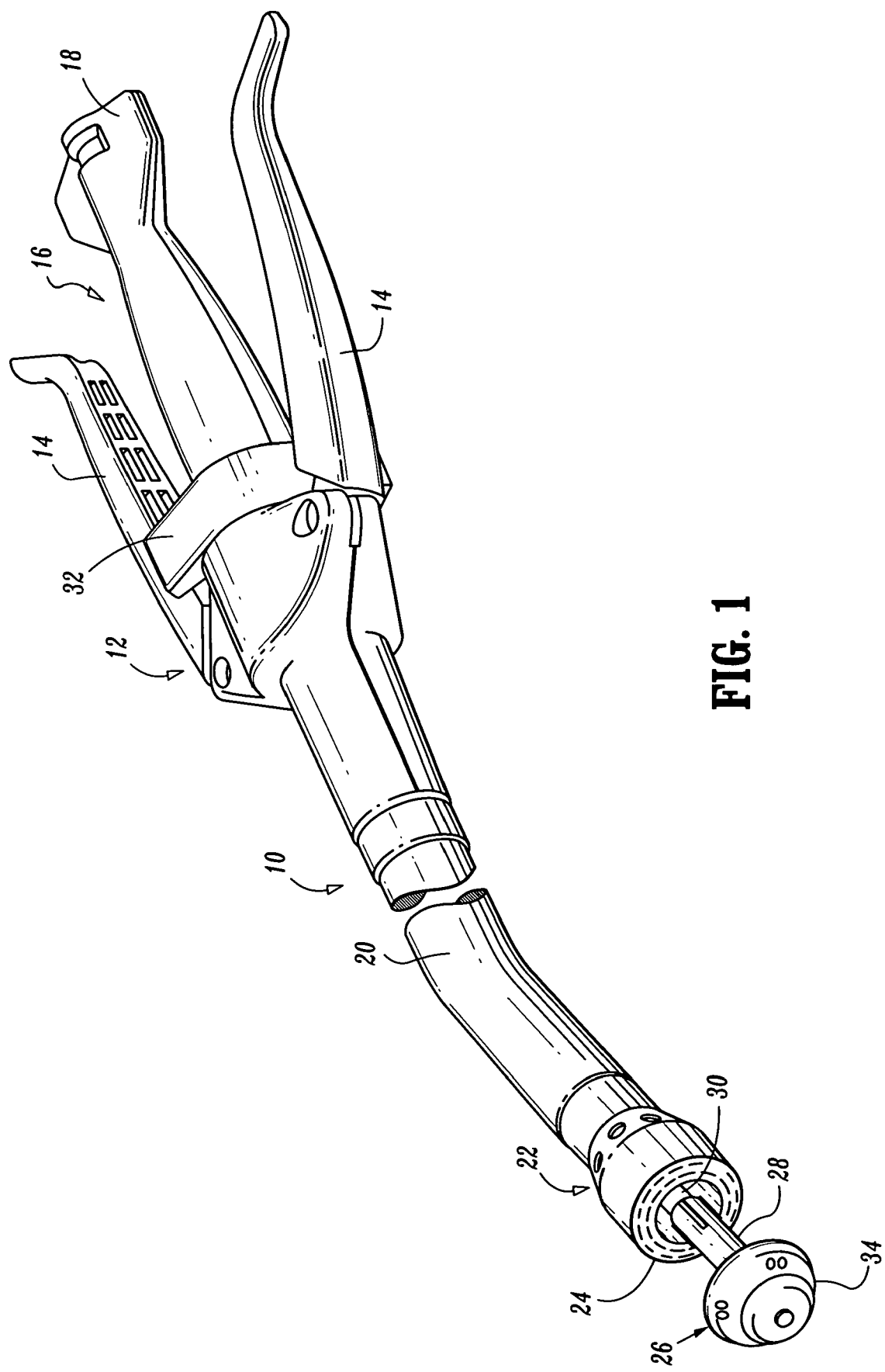
FIG. 1 illustrates a perspective view of a surgical stapling apparatus according to an embodiment of the present disclosure.

Embodiments of the presently disclosed surgical stapling apparatus will now be described in detail with reference to the drawing figures wherein like reference numerals identify similar or identical elements. As used herein and as is traditional, the term "distal" refers to that portion which is furthest from the user while the term "proximal" refers to that portion which is closer to the user.

Referring now in specific detail to the drawings, in which like reference numerals identify similar or identical elements throughout the several views, FIG. 1 shows a surgical stapling apparatus 10 which employs the structure for applying a dispersible adhesive according to the present disclosure. Apparatus 10 includes a handle assembly 12 having at least one pivotable actuating handle member 14, and further includes advancing means 16. Advancing means 16 includes a rotatable grip member 18 whose function will be described below.

Extending from handle assembly 12, there is provided a tubular body portion 20 which may be constructed so as to have a curved shape along at least a portion of its length. Tubular body portion 20 may also be straight, or in other embodiments, tubular body portion 20 may be flexible to bend to any configuration. Body portion 20 terminates in a staple cartridge assembly 22. Staple cartridge assembly 22 includes an annular array of staples "S". Positioned opposite staple cartridge assembly 22 is provided an anvil assembly 26 which is connected to apparatus 10 by shaft 28 at connection means 30. Anvil assembly 26 and staple cartridge assembly 22 are disclosed in commonly assigned U.S. Pat. No. 5,119,983, issued Jun. 9, 1992, which is incorporated herein by reference.

While apparatus 10 is shown and described as utilizing a staple cartridge assembly having an annular array of staples positioned on the tubular body portion, and having the anvil assembly positioned opposite the staple cartridge assembly for movement towards and away from the staple cartridge assembly, it is of course contemplated that the anvil assembly may be positioned on the tubular body portion and the staple cartridge assembly and array of staples be positioned opposite the anvil assembly for movement towards and away from the anvil assembly. Such a construction is to be considered within the scope of the present disclosure.

In operation, apparatus 10 is positioned within a tubular organ in the body of the patient and the ends of the organ to be joined are positioned in the gap between staple cartridge assembly 22 and anvil assembly 26 so that anvil assembly 26 is fully extended. As is conventional, the ends of the organ may be secured over anvil assembly 26 and staple cartridge assembly 22 by a purse string suture prior to approximation of anvil assembly 26 in relation to staple cartridge assembly 22. With anvil assembly; 26 and staple cartridge assembly 22 purse string sutured, stem 28 of anvil assembly 26 is coupled to connection means 30 disposed within staple cartridge assembly 22.

In order to approximate anvil assembly 26 towards staple cartridge assembly 22, grip member 18 is rotated to displace an inner rod member (not shown) in a proximal direction. This draws anvil assembly 26 into position adjacent staple cartridge assembly 22 and locates the ends of the tissue between these two members.

Once the proper distance is set between anvil assembly 26 and staple cartridge assembly 22 interlock means 32 may be released and actuating handles 14 may be pivoted to drive the staples through the tissue and against anvil assembly 26 to complete the circular anastomosis of the tubular organ. Reference may be made to U.S. Pat. No. 5,119,983, previously incorporated herein by reference for a more detailed description and discussion of the structure and operation of surgical stapling apparatus 10.

Figure 2:
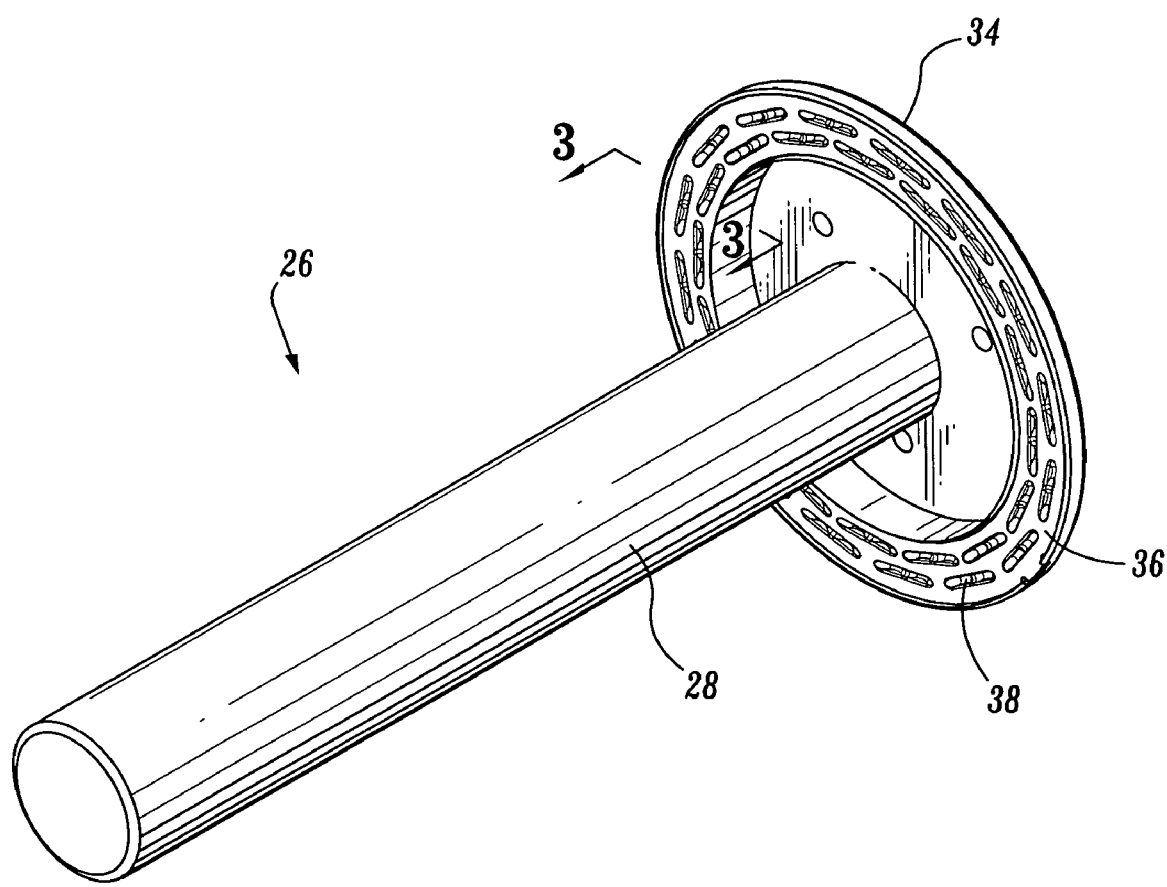
FIG. 2 is a perspective view of an anvil assembly according to an embodiment of the present disclosure.
Figure 3:
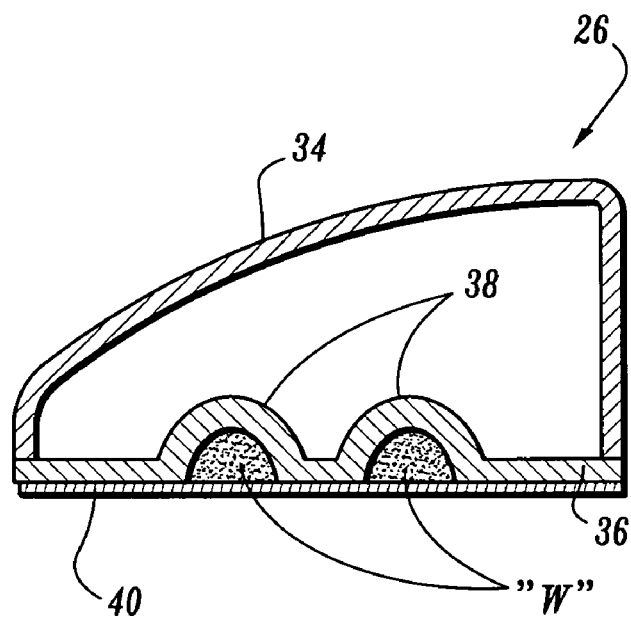
FIG. 3 is a cross-sectional view of the anvil assembly as taken through 3-3 of FIG. 2.

As seen in FIGS. 1-4, anvil assembly 26 includes an anvil head 34 and a stem 28 extending from anvil head 34. Anvil head 34 is configured to support an anvil plate 36 thereon. As seen in FIGS. 2 and 3, anvil plate 36 includes a plurality of staple forming pockets 38 therein. Desirably, staple forming pockets 38 are arranged in a pair of spaced apart concentric annular rings formed in anvil plate 36.

Figure 4:
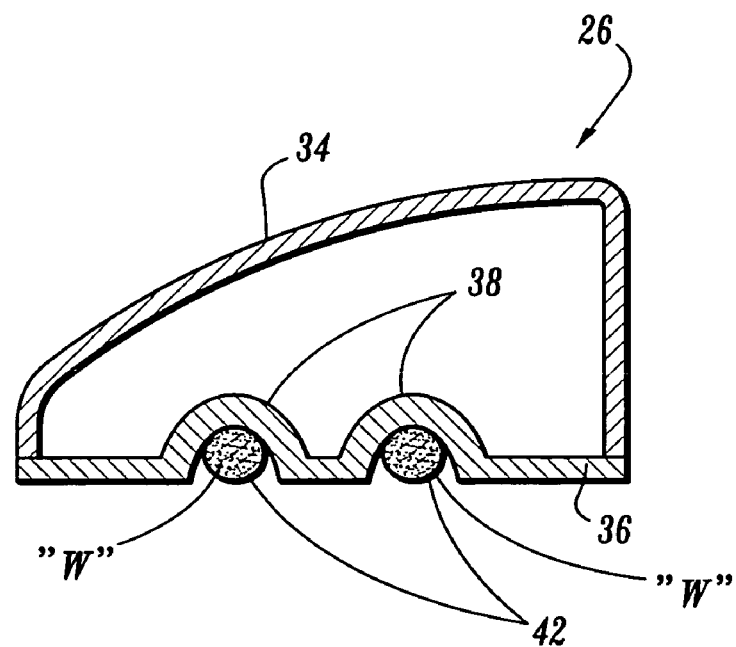
FIG. 4 is a cross-sectional view of an alternate anvil assembly according to the present disclosure, as taken through 3-3 of FIG. 2.

As seen in FIGS. 3 and 4, each staple forming pocket 38 includes a quantity of wound treatment material "W" therein. As seen in FIG. 3, a film or liner 40 may be placed over or onto the surface of anvil plate 36 thereby covering staple forming pockets 38 and retaining the wound treatment material "W" therein. Alternatively, as seen in FIG. 4, the wound treatment material "W" may be contained in a capsule or liquid-gel 42 placed in each staple forming pocket 38. Desirably, each capsule 42 is adhered to or otherwise fixedly contained to staple forming pockets 38.

Desirably, liner 40 is fabricated from a material which may be penetrated or ruptured by surgical staples "S". For example, liner 40 may be fabricated from a polymeric material, such as, polyethylene, polyester, polyurethane and the like. It is envisioned that liner 40 is fabricated from a bioabsorbable material. In this manner, should a portion or all of liner 40 remain in the body following the surgical procedure, that portion of the liner 40 will be absorbed into the body.

Wound treatment material includes and is not limited to an adhesive, sealant, hemostat and/or other medicament. Desirably, in use, the sealant component of the wound treatment material "W" functions to retard any bleeding which may occur from the tissue, and the adhesive component of the wound treatment material "W" functions to secure the approximated tissue together.

It is contemplated that the adhesive includes, and is not limited, to adhesives which cure upon tissue contact, which cure upon exposure to ultraviolet (UV) light, which are pressure sensitive, which are any combinations thereof, or any other known suitable adhesive. In one embodiment, it is contemplated that an adhesive having a cure time of from about 10 to 15 seconds may be used. In another embodiment, it is contemplated that an adhesive having a cure time of about 30 seconds may be used.

It is envisioned that the wound treatment material "W" may be a pre-cured adhesive or sealant. The pre-cured sealant or adhesive will react with the moisture and/or heat of the body tissue to thereby activate the sealing and/or adhesive properties of the sealant or adhesive. It is envisioned that the pre-cured sealant or adhesive may be a hydro-gel or the like.

Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfate, and coagulants.

The wound treatment material "W" may also include medicaments. The medicaments may include one or more medically and/or surgically useful substances such as drugs, enzymes, growth factors, peptides, proteins, dyes, diagnostic agents or hemostasis agents or any other pharmaceutical used in the prevention of stenosis.

Figure 5:
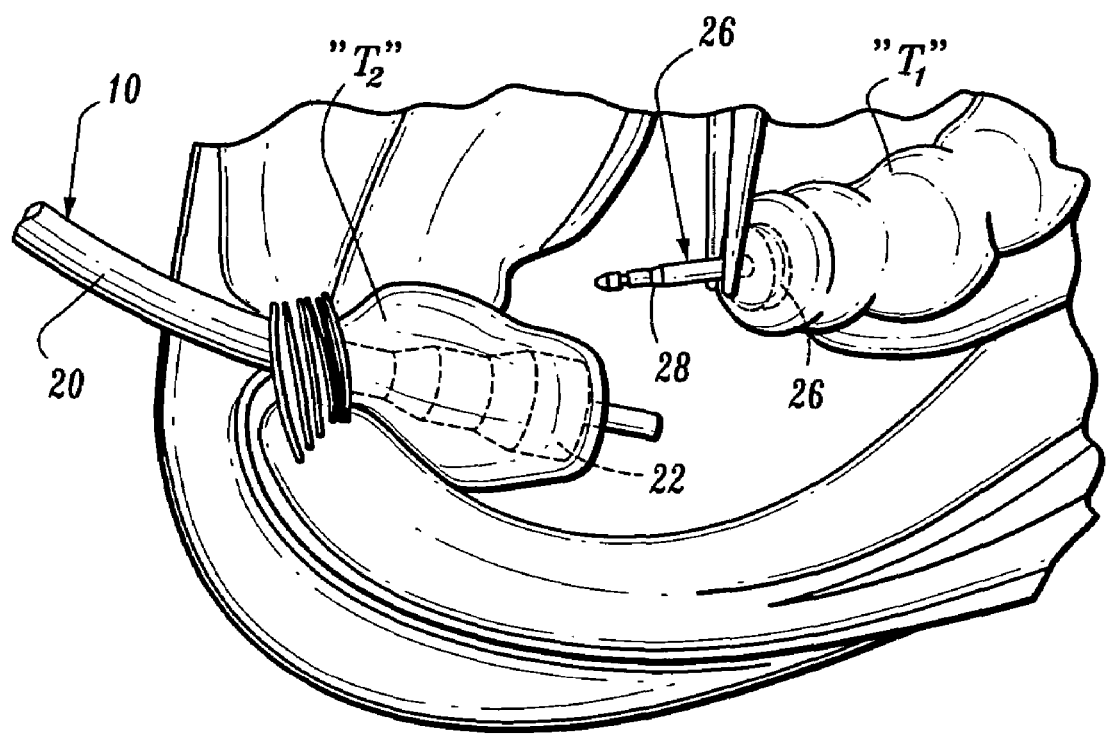
FIG. 5 is a perspective view of the intestinal area of a patient, illustrating a method of positioning the anvil assembly of FIGS. 2-4 in performing an intestinal anastomosis.
Figure 6:
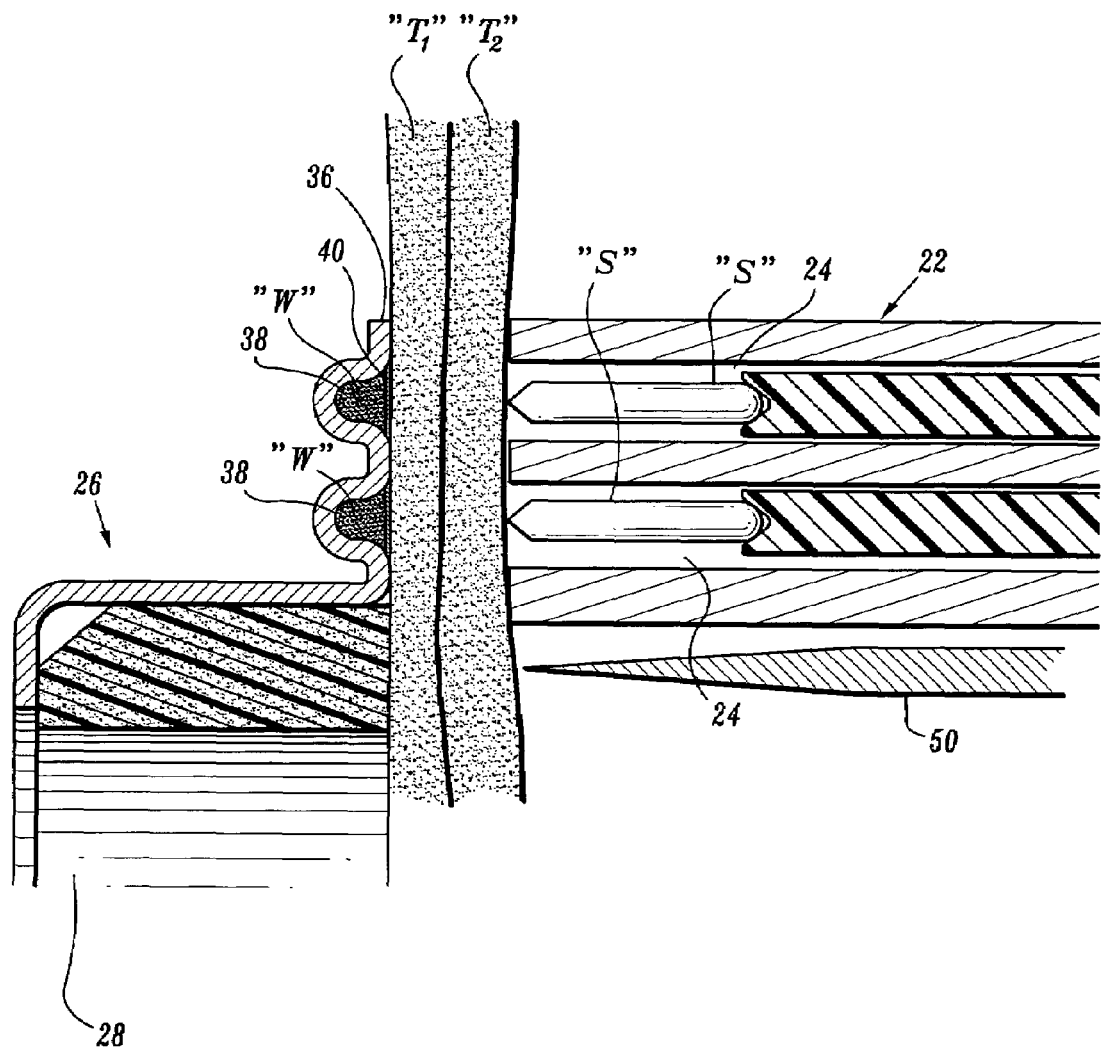
FIG. 6 is an enlarged detail view of the anvil assembly of FIGS. 2-4 and a staple cartridge assembly of the surgical stapling apparatus positioned in the target surgical site immediately prior to the firing of the surgical stapling apparatus.
Figure 7:
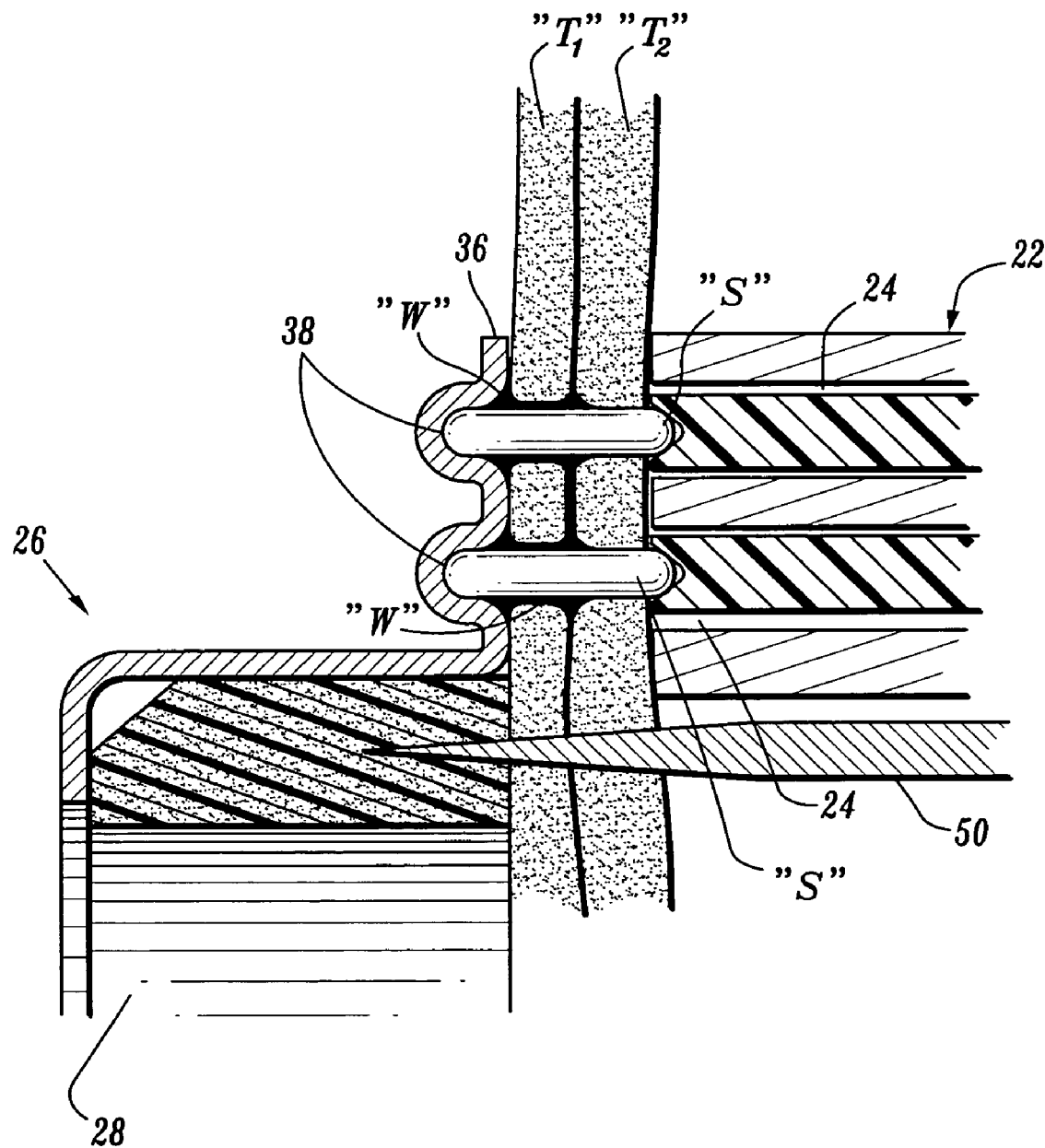
FIG. 7 is an enlarged detail view of the dispensing of the wound treatment material from the anvil assembly upon the firing of the surgical stapling apparatus.

Turning now to FIGS. 5-7, there is illustrated the use of surgical stapling device 10 and detachable anvil assembly 100 in an anastomosis procedure to effect joining of adjacent intestinal sections "T1 and T2". The anastomosis procedure is typically performed using minimally invasive surgical techniques including laparoscopic means and instrumentation. At the point in the procedure shown in FIG. 5, a diseased intestinal section has been previously removed, anvil assembly 26 has been applied to the operative site either through a surgical incision or transanally and positioned within first intestinal section "T1", and tubular body portion 20 of surgical stapling device 10 has been inserted transanally into second intestinal section "T2". Intestinal sections "T1 and T2" are also shown temporarily secured about their respective components (e.g., shaft 28 of anvil assembly 26, and the distal end of tubular body portion 20) by conventional means such as a purse string suture (not shown).

The surgeon then maneuvers anvil assembly 26 until a proximal end of shaft 28 is operatively connected to connection means 30 of tubular body portion 20. Thereafter, anvil assembly 26 and tubular body portion 20 are approximated to approximate intestinal sections "T1 and T2".

Turning now to FIG. 6, with anvil assembly 26 approximated toward staple cartridge assembly 22 and intestinal sections "T1 and T2" clamped or captured therebetween, staple forming pockets 38 of anvil assembly 26 are in registration with staple retaining slots 24 of staple fastener member 22. In particular, staples "S", retained in staple retaining slots 24, are in registration with staple forming pockets 38 of anvil assembly 26.

With anvil assembly 26 so positioned relative to staple cartridge assembly 22, surgical stapling device 10 is fired thereby stapling and adhering intestinal sections "T1 and T2" to one another. As seen in FIG. 7, upon firing of surgical stapling device 10, staples "S" are driven from staple cartridge assembly 22 and driven through intestinal sections "T1 and T2" thereby mechanically securing intestinal sections "T1 and T2" to one another. As staples "S" are driven through intestinal sections "T1 and T2", staples "S" penetrate liner 40 and release wound treatment material "W" contained in staple forming pockets 38 of anvil plate 36 onto intestinal tissue "T2". Desirably, the wound treatment material "W" spreads along staples "S" to the interface between intestinal tissues "T1 and T2". In this manner, if wound treatment material "W" contains an adhesive, the wound treatment material "W" helps to adhere intestinal sections "T1 and T2" to one another.

It is further envisioned that if wound treatment material "W" contains a sealant, the seepage of blood at the or on the anvil side of staple "S" (e.g., in first intestinal tissue "T1") is reduced relative to a surgical apparatus having an anvil assembly with no wound treatment material. In use, as staples "S" are driven into staple forming pockets 38 of anvil assembly 26, the wound treatment material "W", including a sealant, is displaced into the area surrounding staples "S".

Simultaneously therewith, knife 50 severs the portions of intestinal sections "T1 and T2" located radially inward of knife 50.

Figure 8:
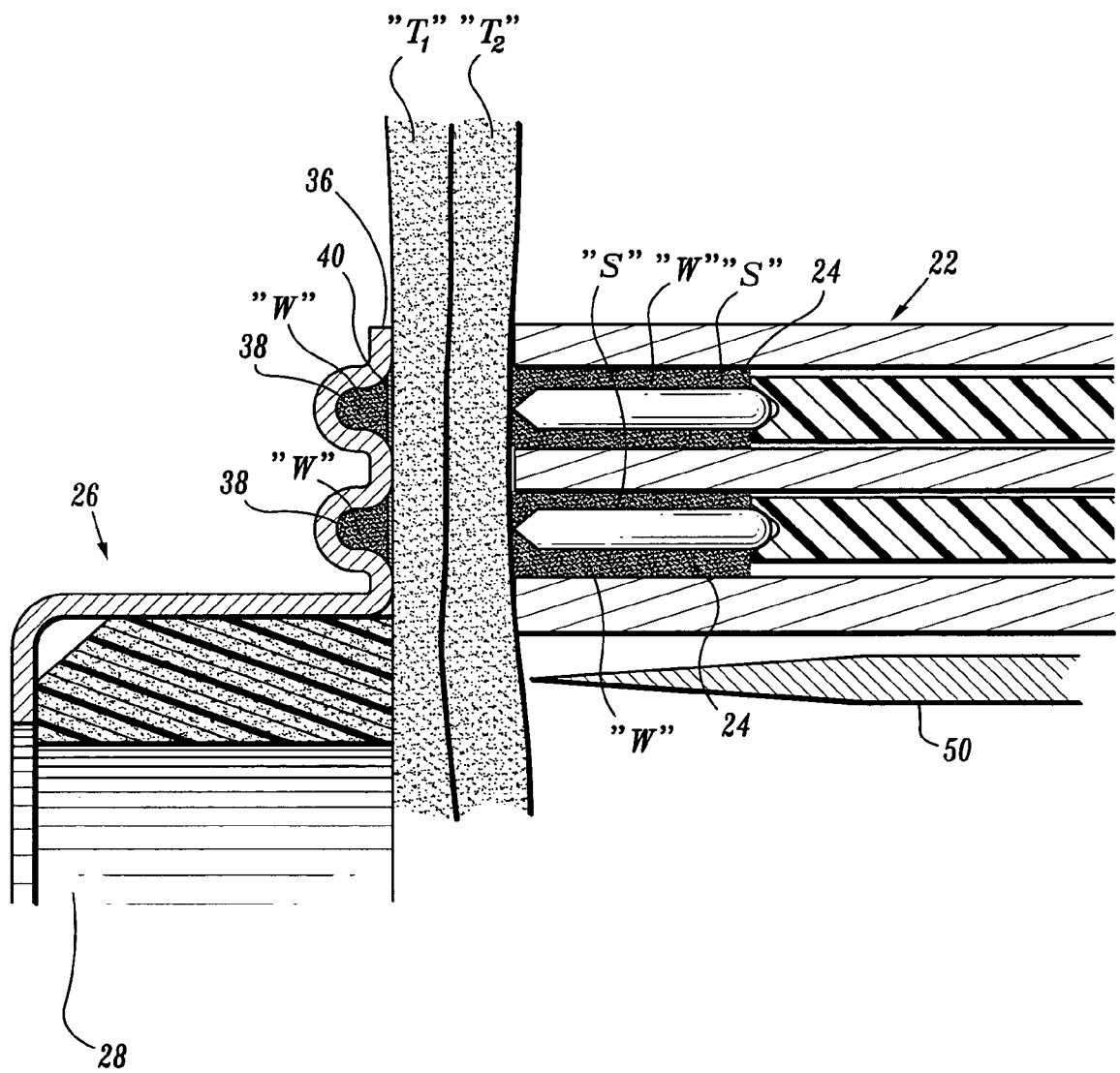
FIG. 8 is an enclosed detail view of the anvil assembly of FIGS. 2-4 and a staple cartridge assembly of a surgical stapling apparatus according to another embodiment of the present disclosure, prior to the filing of the surgical stapling apparatus.

Turning now to FIG. 8, in an alternate embodiment, wound treatment material "W", including a sealant, may be disposed within (e.g., loaded into, packed into, etc.) staple retaining slots 24. Accordingly, in use, when surgical stapling apparatus 10 is fired, the wound treatment material "W" is dispensed onto or otherwise spread onto the area of second intestinal section "T2" surrounding a backspan of staples "S".

While several particular forms of anvil assemblies, and a particular method of using the same, have been illustrated and described, it will also be apparent that various modifications can be made without departing from the spirit and scope of the present disclosure. For example, it is envisioned and within the scope of the present disclosure for an ultraviolet light activated wound treatment material (e.g., adhesive) to be used in staple forming pockets 38 of anvil assembly 26. Accordingly, in use, either prior to or following firing of surgical stapling device 10, the anastombsis site is irradiated with UV light to thereby activate the adhesive.

Thus, it should be understood that various changes in form, detail and application of the anvil assembly of the present disclosure may be made without departing from the spirit and scope of the present disclosure.

What is claimed is:

1. An anvil assembly for a circular stapling apparatus, the anvil assembly comprising:
   an anvil head configured to support an anvil plate thereon;
   a shaft extending from the anvil head and configured to selectively engage a connection member of the circular stapling apparatus;
   the anvil plate operatively connected to the anvil head, the anvil plate defining a plurality of staple forming pockets therein; and
   a wound treatment material disposed within each staple forming pocket of the anvil plate, wherein the wound treatment material is at least one of an adhesive, a sealant, a hemostat and a medicament, wherein the wound treatment material is contained in a capsule, wherein each capsule is configured for retention within the staple forming pockets.

2. The anvil assembly according to claim 1, wherein the wound treatment material is at least one of an adhesive, a sealant, a hemostat and a medicament.

3. The anvil assembly according to claim 2, wherein the adhesive includes at least one of an adhesive which cures upon tissue contact, an adhesive which cures upon exposure to ultraviolet (UV) light, and an adhesive which is pressure sensitive.

4. The anvil assembly according to claim 2, wherein the adhesive includes at least one of a protein derived, aldehyde-based adhesive material, and a cyanoacrylate-based material.

5. The anvil assembly according to claim 2, wherein the sealant material includes at least one of a fibrin sealant material, a collagen-based and synthetic polymer-based tissue sealant material, and synthetic polyethylene glycol-based, hydrogel sealant material.

6. The anvil assembly according to claim 2, wherein the hemostat material includes at least one of a fibrin-based material, a collagen-based material, an oxidized regenerated cellulose-based material, a gelatin-based material, and a fibrinogen-thrombin material.

7. The anvil assembly according to claim 2, wherein the medicament includes at least one of drugs, enzymes, growth factors, peptides, proteins, dyes, and diagnostic agents.

8. The anvil assembly according to claim 2, further comprising a liner covering the plurality of staple forming pockets.

9. The anvil assembly according to claim 8, wherein the staple forming pockets are arranged in a pair of spaced apart concentric annular rings.

10. The anvil assembly according to claim 9, wherein the staple forming pockets are in registration with respective staple retaining slots formed in a staple cartridge assembly of the surgical stapling apparatus.

11. An anvil assembly for a circular stapling apparatus, the anvil assembly comprising:
    an anvil head configured to support an anvil plate thereon;
    a shaft extending from the anvil head and configured to selectively engage a connection member of the circular stapling apparatus;
    the anvil plate operatively connected to the anvil head, the anvil plate defining a plurality of staple forming pockets therein;
    a wound treatment material disposed within each staple forming pocket of the anvil plate, wherein the wound treatment material is at least one of an adhesive, a sealant, a hemostat and a medicament, wherein the wound treatment material is contained in a capsule, wherein each capsule is configured for retention within the staple forming pockets.

12. The surgical stapling apparatus according to claim 11 wherein the wound treatment material is at least one of an adhesive, a sealant, a hemostat and a medicament.

13. The surgical stapling apparatus according to claim 11, wherein the adhesive includes at least one of a protein derived, aldehyde-based adhesive material, and a cyanoacrylate-based material.

14. The surgical stapling apparatus according to claim 11, wherein the sealant material includes at least one of a fibrin sealant material, a collagen-based and synthetic polymer-based tissue sealant material, and synthetic polyethylene glycol-based, hydrogel sealant material.

15. The surgical stapling apparatus according to claim 11, wherein the hemostat material includes at least one of a fibrin-based material, a collagen-based material, an oxidized regenerated cellulose-based material, a gelatin-based material, and a fibrinogen-thrombin material.

16. The surgical stapling apparatus according to claim 11, wherein the medicament includes at least one of drugs, enzymes, growth factors, peptides, proteins, dyes, and diagnostic agents.

* * * * *